(12) United States Patent
Kobayashi et al.

(10) Patent No.: US 11,659,986 B2
(45) Date of Patent: May 30, 2023

(54) OPHTHALMIC APPARATUS, AND RECORDING MEDIUM STORING OPHTHALMIC APPARATUS CONTROLLING PROGRAM

(71) Applicant: NIDEK CO., LTD., Aichi (JP)

(72) Inventors: Shirohisa Kobayashi, Aichi (JP); Kunio Suzuki, Aichi (JP); Hiroyoshi Nakanishi, Aichi (JP); Kazunari Shimizu, Aichi (JP)

(73) Assignee: NIDEK CO., LTD., Aichi (JP)

( * ) Notice: Subject to any disclaimer, the term of this patent is extended or adjusted under 35 U.S.C. 154(b) by 252 days.

(21) Appl. No.: 17/016,931

(22) Filed: Sep. 10, 2020

(65) Prior Publication Data

US 2021/0076927 A1    Mar. 18, 2021

(30) Foreign Application Priority Data

Sep. 13, 2019  (JP) .............................. JP2019-167680

(51) Int. Cl.
*A61B 3/00* (2006.01)
*A61B 3/10* (2006.01)
(Continued)

(52) U.S. Cl.
CPC ............ *A61B 3/0058* (2013.01); *A61B 3/005* (2013.01); *A61B 3/102* (2013.01); *A61B 3/1025* (2013.01); *A61B 3/152* (2013.01); *A61B 3/16* (2013.01)

(58) Field of Classification Search
CPC ....... A61B 3/0058; A61B 3/005; A61B 3/102; A61B 3/1025; A61B 3/152; A61B 3/16; A61B 3/165
(Continued)

(56) References Cited

U.S. PATENT DOCUMENTS

| 5,909,269 A | * | 6/1999 | Isogai | ..................... | A61B 3/152 |
| | | | | | 351/208 |
| 2004/0189936 A1 | * | 9/2004 | Mimura | .................. | A61B 3/165 |
| | | | | | 351/205 |

(Continued)

FOREIGN PATENT DOCUMENTS

| JP | 7-255677 A | 10/1995 |
| JP | 2018-126258 | 8/2018 |
| JP | 2018-126324 | 8/2018 |

OTHER PUBLICATIONS

Japanese Office Action (JPOA) dated Feb. 21, 2023 for the corresponding Japanese Patent Application No. 2019-167680 with its English translation.
(Continued)

*Primary Examiner* — Mohammed A Hasan
(74) *Attorney, Agent, or Firm* — Rankin, Hill & Clark LLP (57) ABSTRACT

Provided is an ophthalmic apparatus for examining an examinee's eye, including: an examination device configured to examine the examinee's eye; an approacher in the examination device, configured to approach the examinee; a detector configured to detect approach of the approacher to the examinee; and a controller configured to switch an operation mode between a first mode where an avoidance operation for avoiding the approach is performed and a second mode where the avoidance operation is not performed, upon the detector detecting the approach.

15 Claims, 7 Drawing Sheets

(51) Int. Cl.
*A61B 3/15* (2006.01)
*A61B 3/16* (2006.01)

(58) Field of Classification Search
USPC .......................................................... 351/206
See application file for complete search history.

(56) References Cited

U.S. PATENT DOCUMENTS

| | | | | |
|---|---|---|---|---|
| 2005/0117116 A1* | 6/2005 | Murakami | ............... | A61B 3/18 |
| | | | | 351/211 |
| 2014/0333896 A1* | 11/2014 | Ueno | ................... | A61B 3/1025 |
| | | | | 351/246 |
| 2017/0347872 A1* | 12/2017 | Ozaki | .................... | A61B 3/152 |

OTHER PUBLICATIONS

Submission of Information for Japanese Patent Application No. 2019-167680 submitted on Mar. 8, 2023 by the third party and its English translation.

FT-1000 Instruction Manual, Dec. 2012, Tomey Corporation Sales Department 1; Cited in Submission of Information for Japanese Patent Application No. 2019-167680.

RT-7000 Instruction Manual, Feb. 10, 2007, Tomey Corporation Sales Department 1; Cited in Submission of Information for Japanese Patent Application No. 2019-167680.

* cited by examiner

OPHTHALMIC APPARATUS, AND RECORDING MEDIUM STORING OPHTHALMIC APPARATUS CONTROLLING PROGRAM

CROSS-REFERENCE TO RELATED APPLICATION

This application claims priority from Japanese Patent Application No. 2019-167680 filed with the Japan Patent Office on Sep. 13, 2019, the entire content of which is hereby incorporated by reference.

BACKGROUND

1. Technical Field

The present disclosure relates to an ophthalmic apparatus for examining an examinee's eye, and a recording medium including an ophthalmic apparatus control program recorded therein.

2. Related Art

For example, an eye refractive power measurement apparatus, a corneal curvature measurement apparatus, an eye pressure measurement apparatus, a fundus camera, OCT (optical coherence tomography) equipment, and an SLO (scanning laser ophthalmoscope) are known as known ophthalmic apparatuses. In these ophthalmic apparatuses, generally, an examination device is moved in up-down, right-left, and front-rear directions with respect to an examinee's eye to align the examination device with a predetermined position for the examinee's eye. Moreover, a proposed apparatus includes a contact sensor for detecting contact to prevent, for example, a nozzle provided to the examination device from contacting the examinee's eye. When the examinee's eye and the examination device contact each other, an avoidance operation is performed (refer to JP-A-7-255677).

SUMMARY

An ophthalmic apparatus for examining an examinee's eye according to an embodiment of the present disclosure includes: an examination device configured to examine the examinee's eye; an approacher in the examination device, configured to approach the examinee; a detector configured to detect approach of the approacher to the examinee; and a controller configured to switch an operation mode between a first mode where an avoidance operation for avoiding the approach is performed and a second mode where the avoidance operation is not performed, upon the detector detecting the approach.

DETAILED DESCRIPTION

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

However, in some cases, depending on the facial shape of an examinee, an examination can be performed only when the examination device is in contact with the examinee. In these cases, the known ophthalmic apparatuses cannot perform an examination since the avoidance operation is repeated whenever the contact sensor detects contact with the examinee.

The present disclosure has been made considering the problem of the known technology. A technical issue of the present invention is to provide an ophthalmic apparatus that can perform an examination without regard to the facial shape of an examinee while ensuring safety, and a recording medium including an ophthalmic apparatus control program recorded therein.

In order to solve the above issue, the present disclosure is characterized by the following configurations:

(1) An ophthalmic apparatus for examining an examinee's eye including: an examination device configured to examine the examinee's eye; an approacher in the examination device, configured to approach the examinee; a detector configured to detect approach of the approacher to the examinee; and a controller configured to switch an operation mode between a first mode where an avoidance operation for avoiding the approach is performed and a second mode where the avoidance operation is not performed, upon the detector detecting the approach.

(2) A recording medium where an ophthalmic apparatus control program to be executed in an ophthalmic apparatus for examining an examinee's eye is recorded, the program being executed by a processor of the ophthalmic apparatus to cause the ophthalmic apparatus to execute: a detection step of detecting approach of an approacher to the examinee, the approacher being configured to approach the examinee in an examination device configured to examine the examinee's eye; and a control step of switching an operation mode between a first mode where an avoidance operation for avoiding the approach is performed and a second mode where the avoidance operation is not performed, upon detecting the approach in the detection step.

According to the present disclosure, it is possible to perform an examination without regard to the facial shape of an examinee, while ensuring safety.

Embodiment

An ophthalmic apparatus according to the present disclosure is described on the basis of the drawings. In the following description, an eye pressure measurement apparatus is taken as an example of the ophthalmic apparatus. The present disclosure can also be applied to other ophthalmic apparatuses such as an eye refractive power measurement apparatus, a corneal curvature measurement apparatus, a cornea shape measurement apparatus, an ocular axial length measurement apparatus, a fundus camera, OCT equipment, and an SLO.

The ophthalmic apparatus of the embodiment measures, for example, the eye pressure of an examinee's eye in a noncontact manner. For example, the ophthalmic apparatus of the embodiment may perform a measurement for each eye, or measure both eyes simultaneously. Moreover, the ophthalmic apparatus may measure only one of the left and right eyes of the examinee.

Figure 1:
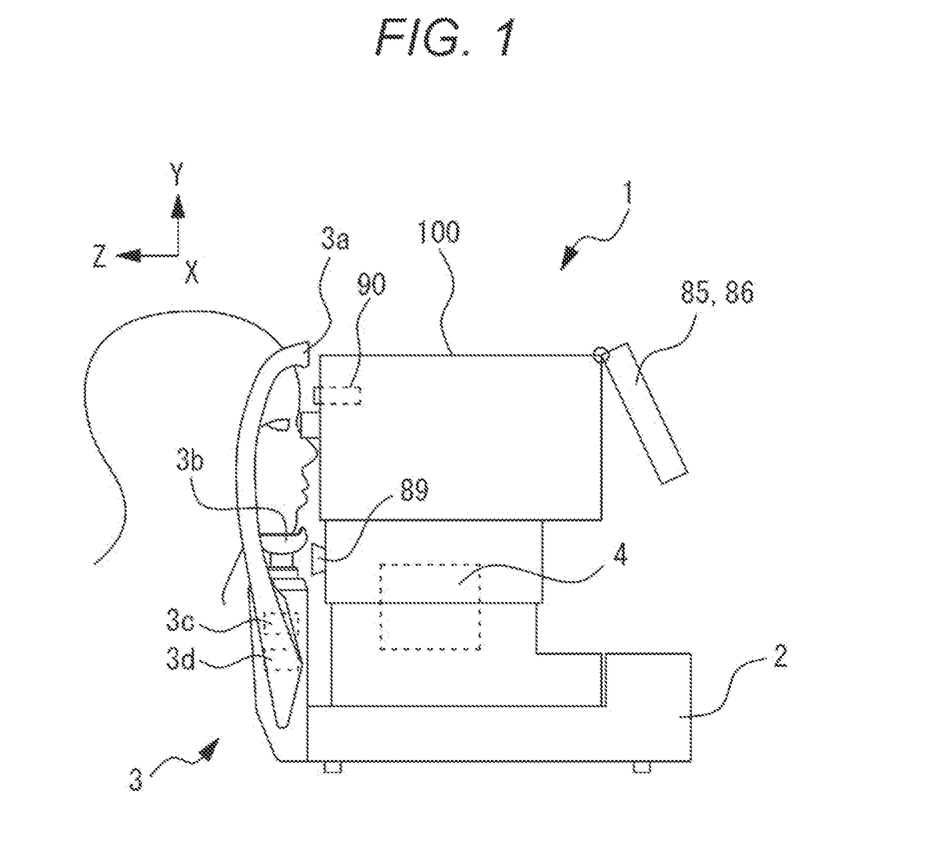
FIG. 1 is a diagram illustrating the external appearance of an ophthalmic apparatus.

As illustrated in FIG. 1, an ophthalmic apparatus 1 of the embodiment includes an examination device 100, a detector 250, and a controller 80. Each configuration is described below.

<Examination Device>

The examination device 100 is an examination device that examines (for example, measures or photographs) an examinee's eye. The examination device 100 includes, for example, a fluid jet device and measuring optical system for measuring the eye pressure of the examinee's eye. Naturally, the examination device 100 may include an optical system that measures the eye's refractive power, the corneal shape, or the like. Moreover, the examination device 100 may include, for example, an optical system for photographing the anterior segment, fundus, or the like of the examinee's eye.

<Fluid Jet Device>

Figure 2:
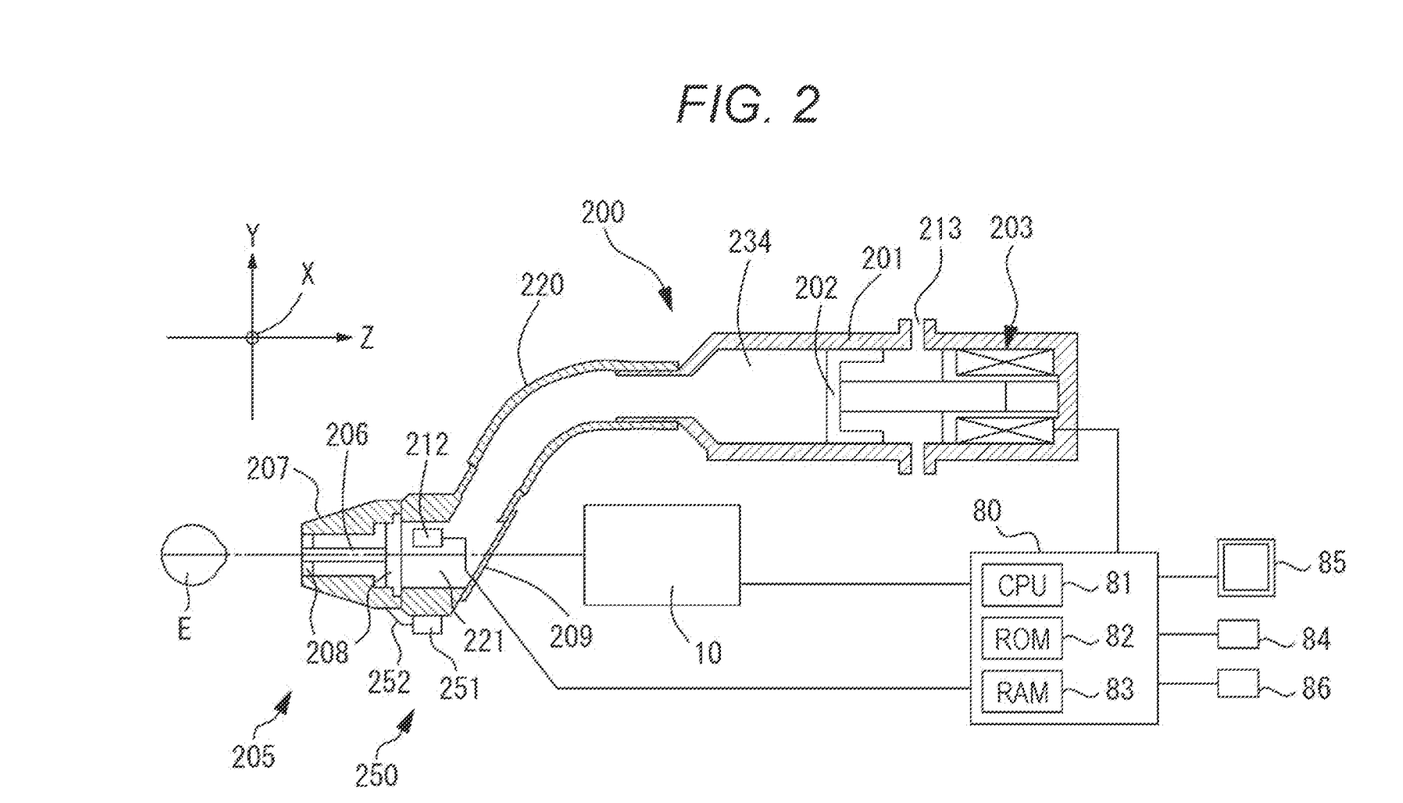
FIG. 2 is a diagram illustrating the internal configuration of the ophthalmic apparatus.

The fluid jet device 200 jets air into the examinee's eye. As illustrated in FIG. 2, the fluid jet device 200 includes, for example, a cylinder 201, a piston 202, a solenoid actuator (hereinafter also referred to as a solenoid) 203, and a nozzle assembly 205. The cylinder 201 and the piston 202 are used as an air compression mechanism that compresses air that is jetted into the examinee's eye. The cylinder 201 is, for example, cylindrical. The piston 202 slides along the axial direction of the cylinder 201. The piston 202 compresses the air of an air compression chamber 234 in the cylinder 201. The solenoid 203 of the embodiment is what is called a direct acting solenoid, and operates linearly. The nozzle assembly 205 includes, for example, a nozzle 206 and a nozzle holder 207. A jet of the compressed air is emitted to the outside of the apparatus through the nozzle 206. The nozzle holder 207 houses the nozzle 206 therein. The nozzle assembly 205 is an approacher that is placed in front of the eye of the examinee and approaches the examinee during measurement.

The air compressed by the travel of the piston 202 in the air compression chamber 234 in the cylinder 201 is jetted through the nozzle 206 and onto the cornea of an examinee's eye E via a tube (or may be a pipe) 220 coupled to an end of the cylinder 201, and an airtight chamber 221 that houses the compressed air. For example, the cylinder 201 may be placed parallel to a horizontal plane (XZ plane). Furthermore, for example, the piston 202 may be caused to travel horizontally in the cylinder 201 by the drive of the solenoid 203 to compress air. For example, the cylinder 201 is placed in such a manner that a longitudinal direction thereof is parallel to the horizontal direction and an inner surface of the cylinder 201 guides the piston 202. Hence, the travel direction (compression direction) of the piston 202 is the horizontal direction. The above constituent members are placed on a stage provided within a housing of the main body of the apparatus.

The fluid jet device 200 may include, for example, a glass plate 208 and a glass plate 209. The glass plate 208 is transparent, and holds the nozzle 206 and transmits observation light and alignment light. The glass plate 209 configures a rear wall of the airtight chamber 221 and transmits the observation light and the alignment light. An observing optical system and alignment optical system is placed behind the glass plate 209 in such a manner that an observation optical axis and alignment optical axis thereof and the axis of the nozzle 206 are coaxial.

The fluid jet device 200 may include, for example, a pressure sensor 212 and an air release hole 213. The pressure sensor 212 detects, for example, the pressure of the airtight chamber 221. The air release hole 213 allows, for example, reducing resistance before the piston 202 gains an initial velocity; therefore, it is possible to obtain a temporally proportional rise pressure change.

<Detector>

The detector 250 is, for example, a detector that detects the contact of the nozzle assembly 205 with the examinee. The detector 250 includes, for example, a contact sensor 251. The contact sensor 251 is, for example, a capacitance sensor. The contact sensor 251 is electrically connected to the nozzle holder 207 by, for example, a wire 252. The contact sensor 251 may be, for example, a pressure-sensitive sensor. In this case, the contact sensor 251 is placed on a surface on the examinee's side of the nozzle assembly 205.

<Measuring Optical System>

Figure 3:
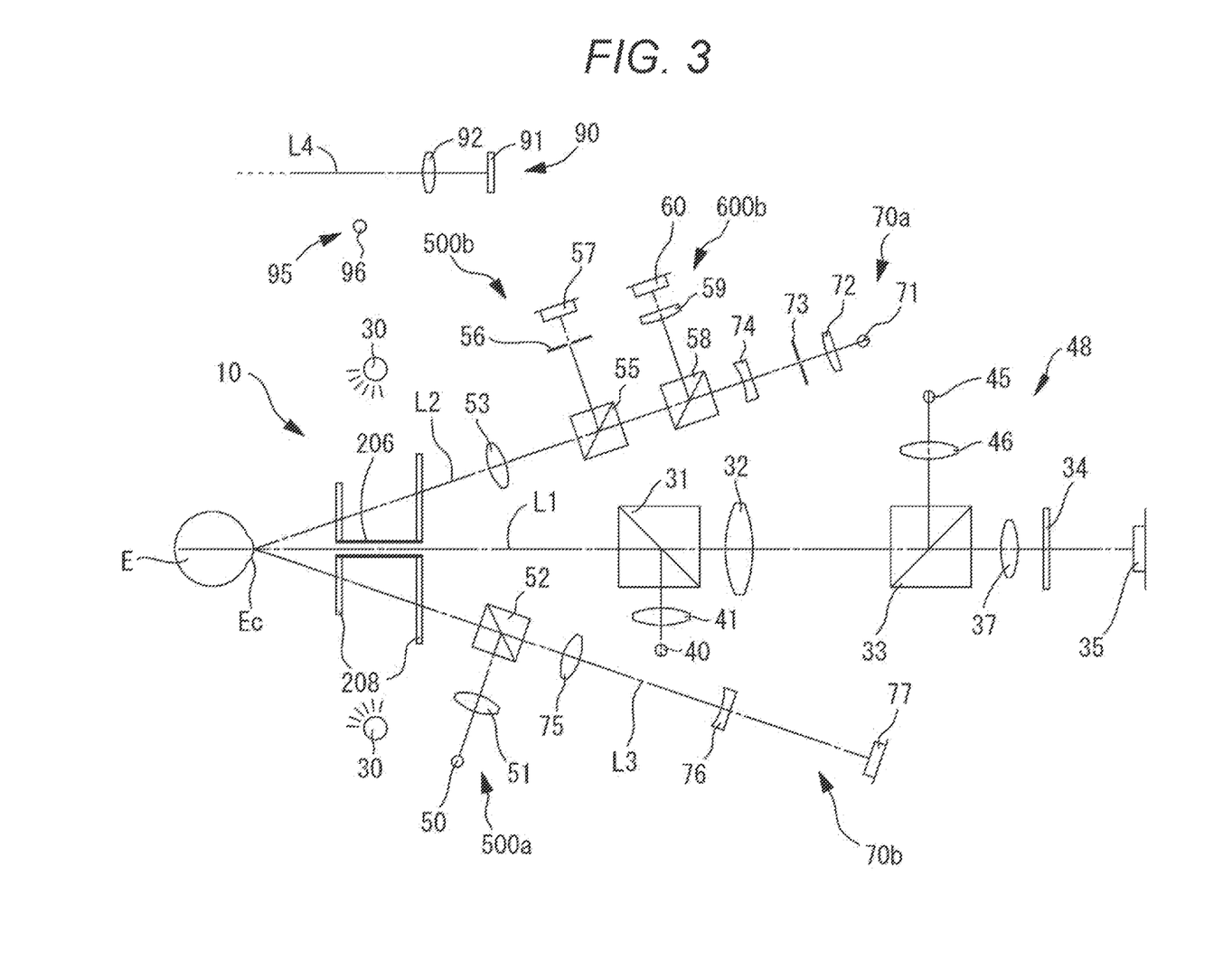
FIG. 3 is a diagram illustrating an optical system of the ophthalmic apparatus.

FIG. 3 is a schematic diagram of a measuring optical system 10 of the ophthalmic apparatus 1. An image of the examinee's eye illuminated by an infrared illuminating light source 30 is formed on a CCD camera 35 via a beam splitter 31, an objective lens 32, a dichroic mirror 33, an imaging lens 37, and a filter 34. In other words, an optical system from the beam splitter 31 to the CCD camera 35 is used as an observing optical system, including an imaging device, for observing the anterior segment of the examinee's eye. In this case, an optical axis L1 is used as an observation optical axis.

The filter 34 has a characteristic that transmits the light of the light source 30 and an infrared light source 40 for alignment, and does not transmit the light of a light source 50 for detecting the deformation of the cornea, which is described below, and visible light. The image formed on the CCD camera 35 is displayed on a display 85.

The infrared light projected from the light source 40 through a projection lens 41 is reflected by the beam splitter 31, and projected onto the examinee's eye from the front. A cornea bright spot formed on the corneal apex by the light source 40 forms an image on the CCD camera 35 via the beam splitter 31 to the filter 34 to be used for alignment detection in the up-down and right-left directions. In other words, the optical system from the beam splitter 31 to the CCD camera 35 is used as a detecting optical system, including an imaging device, for detecting an alignment state with the examinee's eye in the up-down and right-left directions. In this case, the optical axis L1 is used as an alignment optical axis. In the embodiment, the detecting optical system is also used as the observing optical system for observing the anterior segment.

A fixation optical system 48 includes the optical axis L1, and presents a fixation target to the eye E from the front. In this case, the optical axis L1 is used as a fixation optical axis. The fixation optical system 48 includes, for example, a visible light source (fixation lamp) 45, a projection lens 46, and the dichroic mirror 33, and projects, onto the eye E, light for making the eye E fixated in the front direction. A light source such as an LED or laser is used as the visible light source 45. Moreover, for example, other than a pattern light source such as a point light source, a slit light source, or a ring light source, a two-dimensional display such as a liquid crystal display is used as the light source 45.

The visible light emitted from the light source 45 passes through the projection lens 46, is reflected by the dichroic mirror 33, passes through the objective lens 32, and then is projected onto the fundus of the eye E. Consequently, the eye E enters a state of fixating a fixation point in the front direction to fix the direction of the visual line. The visible light emitted from the light source 45 passes through the projection lens 46 and the objective lens 32 to be converted to a parallel light flux.

A cornea deformation detecting optical system includes a light projecting optical system 500a and a light receiving optical system 500b, and is used to detect the deformed state of a cornea Ec. The optical systems 500a and 500b are placed in the examination device 100, and moved three-dimensionally by a driver 4.

The light projecting optical system 500a includes an optical axis L3 as a light projecting optical axis, and applies illuminating light to the cornea Ec of the eye E from an oblique angle. The light projecting optical system 500a includes, for example, the infrared light source 50, a collimator lens 51, and a beam splitter 52. The light receiving optical system 500b includes a photodetector 57, and receives reflected light of the illuminating light from the cornea Ec of the eye E. The light receiving optical system 500b is placed in such a manner as to be substantially symmetric about the optical axis L1 with respect to the light projecting optical system 500a. The light receiving optical system 500b includes, for example, a lens 53, a beam splitter 55, a pinhole plate 56, and the photodetector 57, and forms an optical axis L2 as a light receiving optical axis.

The light emitted from the light source 50 is rendered into a substantially parallel light flux by the collimator lens 51, and reflected by the beam splitter 52. The light then becomes coaxial (agrees) with the optical axis L3 of a light receiving optical system 70b described below, and is projected onto the cornea Ec of the examinee's eye. The light reflected from the cornea Ec becomes coaxial (agrees) with the optical axis L2 of a light projecting optical system 70a described below, and passes through the lens 53. The light is then reflected by the beam splitter 55, passes through the pinhole plate 56, and is received on the photodetector 57. The lens 53 is covered with a coating having a characteristic that does not transmit the light from the light sources 30 and 40. Moreover, the optical system for detecting the deformation of the cornea is placed in such a manner as to maximize the amount of received light of the photodetector 57 when the examinee's eye is in a predetermined deformed state (flattened state).

Moreover, the cornea deformation detecting optical system also serves as a part of a first working distance detecting optical system. A light projecting optical system of the first working distance detecting optical system also serves as the light projecting optical system 500a of the cornea deformation detecting optical system. A light receiving optical system 600b that receives the light of the light source 50 reflected from the cornea Ec includes, for example, the lens 53 of the light receiving optical system 500b, a beam splitter 58, a condenser lens 59, and a position-sensitive device 60, and forms the optical axis L2 as the light receiving optical axis.

The illuminating light projected from the light source 50 and reflected from the cornea Ec forms a target image being a virtual image of the light source 50. The light of the target image passes through the lens 53 and the beam splitter 55, and is reflected by the beam splitter 58. Furthermore, the light passes through the condenser lens 59, and enters the one-dimensional or two-dimensional position-sensitive device 60 such as a PSD or line sensor. In terms of the position-sensitive device 60, when the examinee's eye E (the cornea Ec) moves in a working distance direction (Z direction), the target image by the light source 50 also moves over the position-sensitive device 60. Hence, a control circuit 20 obtains working distance information on the basis of an output signal from the position-sensitive device 60. The output signal from the position-sensitive device 60 according to the embodiment is used for alignment (rough adjustment) in the working distance direction (Z direction). The light receiving optical system 600b of the first working distance detecting optical system uses a lower magnification than the light receiving optical system 70b described below. Hence, the distance detection range of the position-sensitive device 60 in the Z direction is longer than a light receiving device 77.

A corneal thickness measuring optical system includes the light projecting optical system 70a, the light receiving optical system 70b, and the fixation optical system 48, and is used to measure the corneal thickness of the examinee's eye E. Moreover, the light projecting optical system 70a also uses the cornea deformation detecting optical system and the first working distance detecting optical system partially.

The light projecting optical system 70a includes the optical axis L2 as a light projecting optical axis, and applies illuminating light (measurement light) to the cornea Ec of the eye E from an oblique angle. The light projecting optical system 70a includes, for example, an illuminating light source 71, a condenser lens 72, a light restricting member 73, a concave lens 74, and the lens 53 shared with the cornea deformation detecting optical system. A visible light source or infrared light source (including near-infrared) is used as the illuminating light source 71. For example, a light source such as an LED or laser is used. The condenser lens 72 concentrates light emitted from the light source 71. The light sources 50 and 71 use a wavelength band.

The light restricting member 73 is placed on the optical path of the light projecting optical system 70a, and restricts the light emitted from the light source 71. The light restricting member 73 is placed at a position substantially conjugated with the cornea Ec. For example, a pinhole plate or slit plate is used as the light restricting member 73. The light restricting member 73 is used as an aperture that passes a part of the light emitted from the light source 71 and blocks the other part of the light. The light projecting optical system 70a forms a predetermined pattern light flux (for example, a spot light flux or slit light flux) on the cornea of the eye E.

The light receiving optical system 70b includes the light receiving device 77, and receives reflected light of the illuminating light from the front and back surfaces of the cornea of the eye E. The light receiving optical system 70b is placed in such a manner as to be substantially symmetric about the optical axis L1 with respect to the light projecting optical system 70a. The light receiving optical system 70b includes, for example, a light receiving lens 75, a concave lens 76, and the light receiving device 77, and forms the optical axis L3 as a light receiving optical axis. The light receiving optical system 70b in FIG. 3 is also used as a second working distance detecting optical system that detects an alignment state with the eye E in the Z direction.

The light receiving device 77 includes a plurality of photoelectric conversion elements, and receives light reflected from the front and back surfaces of the cornea. A photo-detection device such as a one-dimensional line sensor or a two-dimensional area sensor is used as the light receiving device 77. The light receiving optical system 70b of the corneal thickness measuring optical system and the second working distance detecting optical system performs observations, using a higher magnification. Hence, the distance detection range of the light receiving device 77 in the Z direction is reduced as compared to the position-sensitive device 60.

When the examinee's eye E (the cornea Ec) moves in the working distance direction (Z direction), the light of the light source 71 reflected from the cornea Ec also moves over the light receiving device 77. Hence, the controller 80 obtains working distance information on the basis of an output signal from the light receiving device 77 of the second working distance detecting optical system. Moreover, the controller 80 finds the cornea deformation state and the blink of the examinee's eye E on the basis of the output signal from the light receiving device 77, and controls the drive of the solenoid 203.

The light emitted from the illuminating light source 71 is concentrated by the condenser lens 72, and illuminates the light restricting member 73 from the back. The light from the light source 71 is restricted by the light restricting member 73. The lens 53 then forms an image by the light (concentrates the light) near the cornea Ec. For example, a pinhole image (if a pinhole plate is used), or a slit image (if a slit plate is used) is formed near the cornea Ec. At this point in time, the light from the light source 71 forms an image near a portion of intersection with the visual axis on the cornea Ec.

When the light projecting optical system 70a projects the illuminating light onto the cornea Ec, the reflected light of the illuminating light from the cornea Ec travels in a direction that is symmetric about the optical axis L1 with respect to the light projecting light flux. The light receiving lens 75 forms an image by the reflected light on a light receiving surface on the light receiving device 77.

The lens 53 shared by the light receiving optical systems 500b and 600b, and the light projecting optical system 70a is placed at a position where the light of the light source 50 reflected from the cornea Ec is concentrated at a center portion of a hole of the pinhole plate 56, and the illuminating light from the light source 71 is concentrated on the front and back surfaces of the cornea Ec.

<Face Photographing Device>

A face photographing device 90 is, for example, an optical system for photographing the face including at least one of the left and right eyes of the examinee. For example, as illustrated in FIG. 3, the face photographing device 90 of the embodiment mainly includes, for example, an imaging device 91 and an imaging lens 92.

The face photographing device 90 is provided, for example, at a position where both eyes of the examinee can be photographed when the examination device 100 is at an initial position. In the embodiment, the initial position of the examination device 100 is set at a position that is off the optical axis L1 of the examination device 100 to the right to easily examine the right eye. Therefore, the face photographing device 90 is provided at a position where both eyes of the examinee can be photographed in a state where the examination device 100 is at the initial position that is off to the right. For example, the face photographing device 90 is placed at the machine center in the state where the examination device 100 is at the initial position. If the initial position is set on the basis of, for example, half-pupillary distance, that is, monocular pupillary distance, the face photographing device 90 may be placed at a position that is a monocular pupillary distance off the machine center of the apparatus main body to the left or right.

The face photographing device 90 of the embodiment, together with the examination device 100, is moved by the driver 4. Naturally, the face photographing device 90 may be configured in such a manner as to be fixed to a base 2 and immovable.

The imaging lens 92 may be, for example, a wide-angle lens. The wide-angle lens is, for example, a fisheye lens or axicon lens. If being provided with the wide-angle lens, the face photographing device 90 can photograph the face of the examinee with a wide angle of view.

<Face Illuminating Optical System>

A face illuminating optical system 95 illuminates the face of the examinee. The face illuminating optical system 95 includes, for example, an illuminating light source 96. The illuminating light source 96 emits infrared light. In the embodiment, the illuminating light source 96 is provided on each of the left and right sides of an optometric window. A light source with lower directivity than the target light source for alignment is used as the face illuminating optical system 95.

<Control System>

As illustrated in FIG. 2, the apparatus 1 includes the controller 80. The controller 80 is responsible for various types of control over the apparatus 1. The controller 80 includes, for example, a general CPU (Central Processing Unit) 81, a ROM 82, and a RAM 83. For example, a recording medium where an ophthalmic apparatus control program for controlling the ophthalmic apparatus 1 is recorded, and initial values are stored in the ROM 82. For example, various kinds of information are temporarily stored in the RAM 83. The controller 80 is connected to the examination device 100, the face photographing device 90, the driver 4, the display 85, an operating device 86, a chin rest driver 3d, a storage (for example, a nonvolatile memory) 84, an audio output device 89, and the like. The storage 84 is, for example, a non-transitory storage medium that can retain stored contents even if the power supply is shut down. For example, a hard disk drive, or detachable USB flash memory can be used as the storage 84.

As illustrated in FIG. 1, the ophthalmic apparatus 1 may include the base 2, a face supporter 3, the driver 4, the display 85, the audio output device 89, and the face photographing device 90. The base 2 supports the examination device 100 movably. The face supporter 3 supports the face of the examinee. The face supporter includes a forehead rest 3a, a chin rest 3b, a chin rest sensor 3c, and the chin rest driver 3d. The chin rest sensor 3c detects whether or not the chin is placed on the chin rest 3b. The chin rest driver 3d moves the chin rest 3b up and down to adjust the height of the chin rest 3b. The driver 4 moves the examination device 100 in the XYZ directions (three-dimensional directions) with respect to the base 2. The display 85 displays, for example, an observation image and measurement result of the examinee's eye. The display 85 may be provided, for example, integrally with the apparatus 1, or separately from the apparatus. The display 85 may be able to be placed in such a manner as to point a display screen thereof not only at, but also toward, the examinee. The display 85 may be used as the operating device 86. In this case, the display 85 is used for various settings of the apparatus 1 and operations at the start of measurement. Various operation instructions of an examiner or examinee are inputted into the display 85. Various human interfaces such as a joystick, mouse, keyboard, trackball, and button may be used as the operating device 86. The face photographing device 90 photographs, for example, the face of the examinee. The audio output device 89 makes an audio announcement to the examinee or examiner. The audio output device 89 is, for example, a speaker. The face photographing device 90 photographs, for example, the face including at least one of the left and right eyes of the examinee.

<Control Operation>

Figure 4:
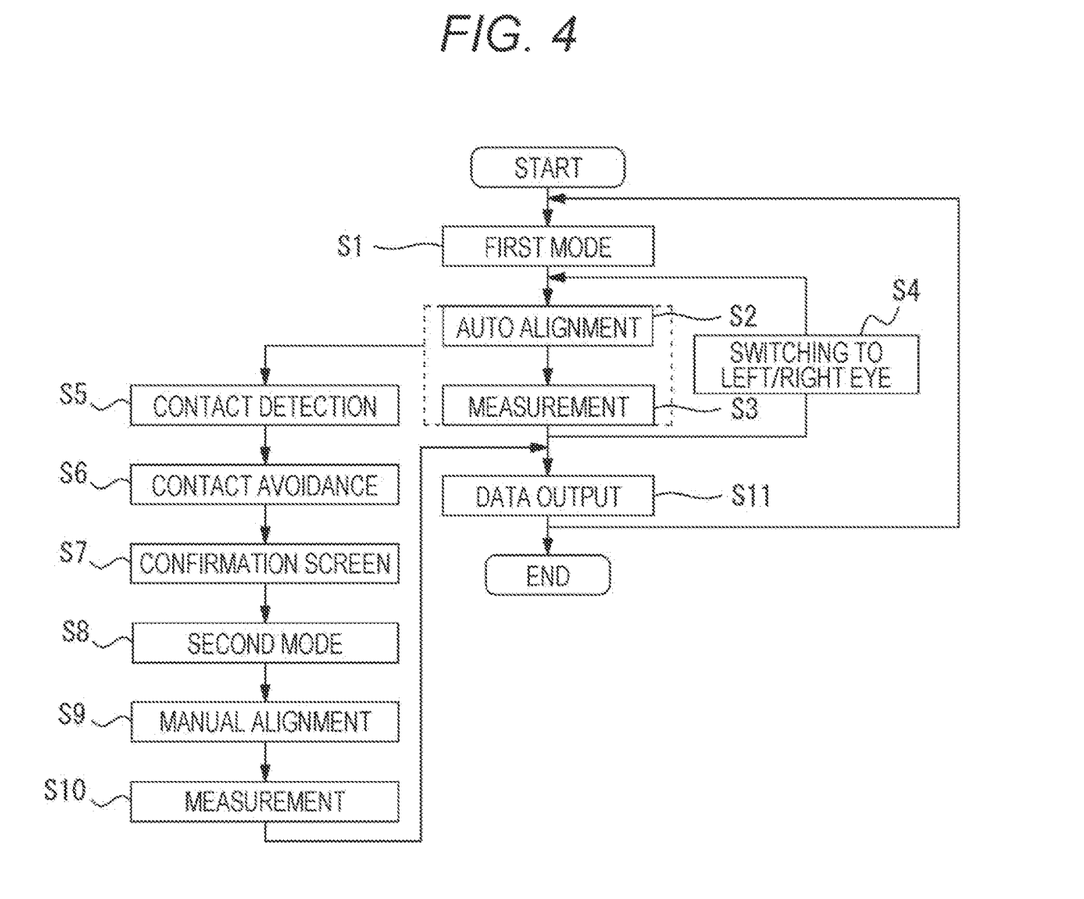
FIG. 4 is a flowchart illustrating the control operation of the ophthalmic apparatus.

The control operation of the ophthalmic apparatus 1 including the above configuration is described on the basis of FIG. 4. The ophthalmic apparatus 1 of the embodiment is provided with two operation modes: a first mode for performing a contact avoidance operation when the detector 250 detects contact between the nozzle assembly 205 and the examinee, and a second mode for not performing the contact avoidance operation. The contact avoidance operation is, for example, the operation of stopping the examination device 100 moving, the operation of causing the examination device 100 to move away from the examinee's eye, or the operation of a combination thereof.

Firstly, the controller 80 sets the operation mode to the first mode (step S1). Naturally, this setting may be configured as an initial value. When the face of the examinee is placed on the face supporter 3, the controller 80 detects that the face has been placed on the face supporter 3, by means of the chin rest sensor 3c. Furthermore, the controller 80 detects both eyes of the examinee from a face image taken by the face photographing device 90. Examples of a method for detecting an examinee's eye from an image include various image processing methods such as pupil detection by infrared photography and luminance edge detection. For example, if an infrared image of the face of the examinee is taken, the skin looks white and the pupil looks black. Therefore, the controller 80 may detect a round black (low brightness) portion as the pupil from the infrared image obtained by infrared photography. The controller 80 detects the examinee's eye from the face image, using the above method, and acquires two-dimensional position information thereof.

After detecting the examinee's eye, the controller 80 starts aligning the examination device 100 in Auto mode (step S2). The Auto mode is, for example, an alignment mode where the controller 80 controls the driver 4, moves the examination device 100 automatically, and accordingly performs an alignment with the examinee's eye. For example, the controller 80 moves the examination device 100 in a direction where the examinee's eye has been detected in the face image. For example, the controller 80 moves the examination device 100 in the direction where the eye has been detected until the examinee's eye appears in an anterior segment image taken by the observing optical system. After the examinee's eye appears in the anterior segment image, the alignment of the examination device 100 is performed on the basis of a bright spot appearing in the anterior segment image.

After completing the alignment, the controller 80 measures the examinee's eye (step S3). For example, the controller 80 measures the corneal thickness of the examinee's eye with the corneal thickness measuring optical system. The controller 80 calculates the distance between a reflected signal from the corneal anterior surface and a reflected signal from the corneal posterior surface (a peak-to-peak distance), the reflected signals having been detected by the light receiving device.

After completing the measurement of the corneal thickness, the controller 80 measures the eye pressure. For example, the controller 80 drives the solenoid 203, and moves the piston 202. Consequently, the air in the cylinder 201 is compressed. The compressed air is blown toward the cornea Ec from the nozzle 206. The cornea Ec deforms gradually due to the blowing of the compressed air. When the cornea Ec has reached a flattened (applanated) state, the maximum amount of light enters the photodetector 57. The controller 80 obtains an eye pressure value on the basis of an output signal from the pressure sensor 212 and an output signal from the photodetector 57. The measurement result is displayed on the display 85. When a predetermined end-of-measurement condition is satisfied, the eye pressure measurement for the examinee's eye is completed.

When both eyes are measured, the controller 80 moves the examination device 100 to the eye that has not yet been measured (step S4: switching to left/right eye). For example, the controller 80 places the examination device 100 in front of the left eye after measuring the right eye. The left eye is then measured as in the right eye.

Figure 5A:
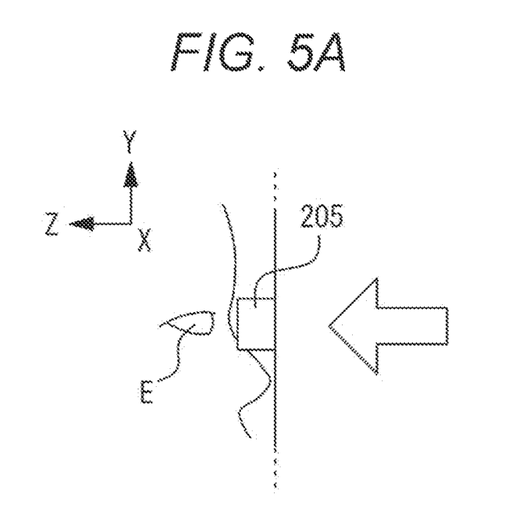
FIGS. 5A and 5B are diagrams illustrating the withdrawal operation of the ophthalmic apparatus.
Figure 5B:
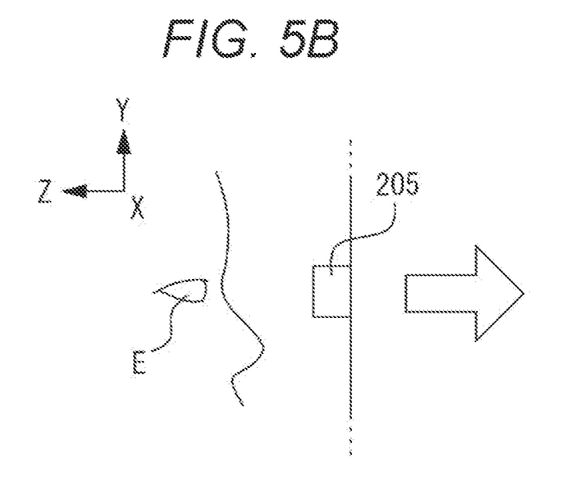

If the detector 250 detects contact between the nozzle assembly 205 and the examinee during the alignment of the examination device 100, or the measurement (step S5), the controller 80 controls the driver 4 to electrically perform the contact avoidance operation (Step S6). For example, the controller 80 moves the examination device 100 back in a direction away from the examinee in terms of the Z direction as illustrated in FIG. 5B from the state where the nozzle assembly 205 and the examinee are in contact with each other as illustrated in FIG. 5A, and then stops the examination device 100.

Figure 6:
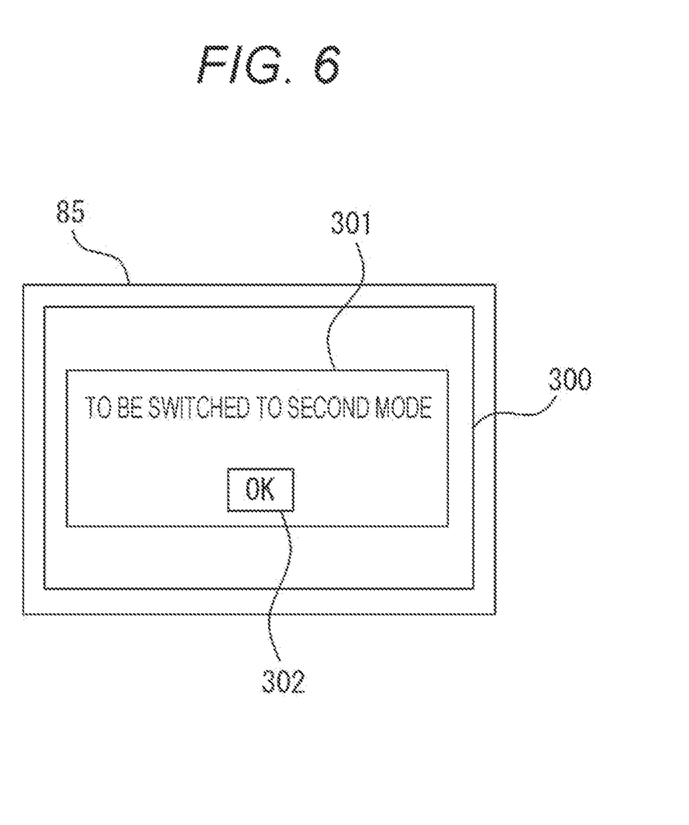
FIG. 6 is a diagram illustrating an example of a display screen of the ophthalmic apparatus.

After performing the contact avoidance operation, the controller 80 displays a confirmation screen 301 for confirming switching to the second mode (that is, turning off the contact avoidance operation) on a screen 300 of the display 85 as illustrated in FIG. 6 (step S7). Consequently, the examiner can perceive that the avoidance operation is not performed, and grasp that a measurement should be performed more carefully. Moreover, the controller 80 may display, on the confirmation screen 301, a confirmation button 302 signifying that the displayed content has been confirmed. In this case, the controller 80 turns off the contact avoidance operation at the press of the confirmation button 302 by the examiner (step S8). Consequently, it is possible to prevent switching to the second mode against the examiner's will (accidentally). Instead of displaying the confirmation screen 301, an audio announcement to the effect that the contact avoidance operation is to be turned off may be made by controlling the audio output device 89. Alternatively, both of the display of the confirmation screen 301 and the audio announcement may be performed.

When the contact avoidance operation is turned off, the controller 80 switches the alignment mode from the Auto mode to a manual mode (step S9), which saves the examiner the time and effort to change the alignment mode. If the alignment mode is the manual mode right from the beginning, the manual mode continues to be maintained. The manual mode is a mode where the examiner aligns the examination device 100 manually. However, the manual mode is not required to be a fully manual mode, and may be a mode where an alignment, tracking, or a measurement is performed automatically at the time when an alignment is completed to some degree (in other words, may include a semi-auto mode).

The examiner then performs a measurement in a state where the second mode has been set (step S10). For example, the controller 80 controls the driver 4 and moves the examination device 100 on the basis of the examiner's operation of the operating device 86, and performs a measurement in the state where the examinee and the nozzle assembly 205 are in contact with each other. If the second mode is set, the contact avoidance operation is turned off.

Figure 7:
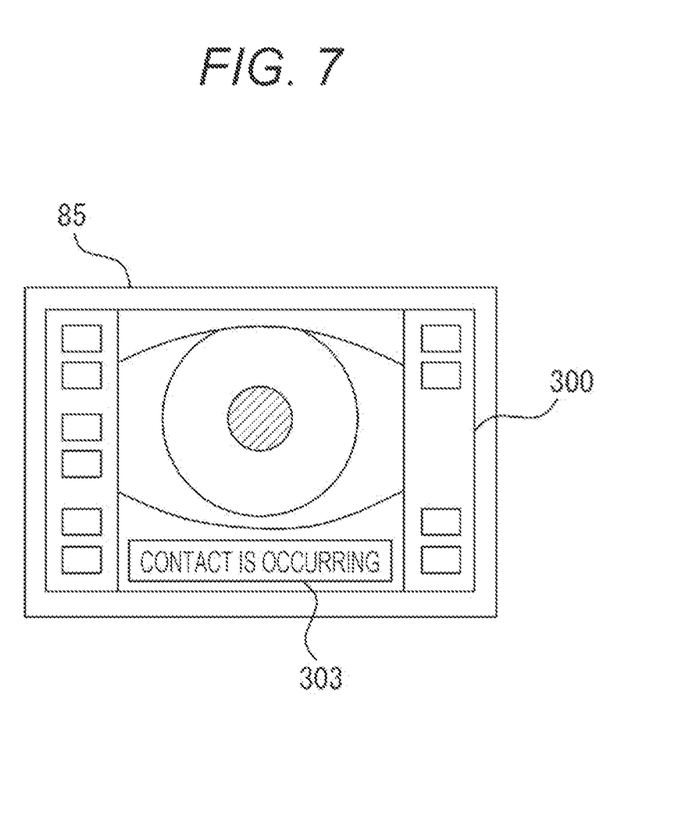
FIG. 7 is a diagram illustrating an example of the display screen of the ophthalmic apparatus.

However, the detector 250 is in operation. In other words, the second mode of the embodiment is an operation mode where even if the detector 250 detects contact, the contact avoidance operation is not performed. For example, if the detector 250 detects contact between the examinee and the nozzle assembly 205, the controller 80 may display information that contact has occurred, or is occurring, as a notification screen 303 on the display 85 as illustrated in FIG. 7, or may cause the audio output device 89 to emit a sound. The examiner views the notification screen 303 and accordingly can grasp that a measurement should be performed more carefully. Naturally, in the second mode, the function of the detector 250 may be turned off in order not to detect contact.

The controller 80 may maintain the second mode for measurement of the same examinee. For example, if both eyes are measured, when contact with one of the examinee's eyes is detected, and then the mode is switched to the second mode, the controller 80 may measure the other of the examinee's eyes, remaining in the second mode. Assume that a human face is substantially symmetric. When the nozzle assembly 205 contacts the face during measurement of one of the examinee's eyes, the nozzle assembly 205 is highly likely to contact the face during measurement of the other of the examinee's eyes. Hence, a measurement can be performed more smoothly by maintaining the second mode rather than taking the trouble to return to the first mode.

After completing the measurement, the controller 80 outputs measurement result data (step S11). For example, the controller 80 displays the measurement result on the display 85, prints out the measurement result, or outputs the measurement result to the outside of the apparatus in a wired or wireless manner. After completing the data output, the controller 80 returns to the process of step S1, and switches the operation mode from the second mode to the first mode (that is, turns on the contact avoidance operation) for the next examinee.

As described above, the ophthalmic apparatus 1 of the embodiment performs the avoidance operation when the detector 250 detects contact between a part of the examination device 100 (for example, the nozzle assembly 205) and the examinee, and accordingly can perform a measurement safely. Moreover, for example, in a case of an examinee with a chiseled face, a part of the examination device 100 may contact the face (for example, the nose or eyebrow) without regard to correct alignment. In terms of this, it is possible to prevent the repeated contact avoidance operation from making it impossible to perform a measurement by switching to the setting where the contact avoidance operation is not performed.

The detector 250 is not limited to detecting contact between the nozzle assembly 205 and the examinee by means of the contact sensor 251. For example, the detector 250 may detect that the nozzle assembly 205 and the examinee approach each other more than necessary by means of a distance measurement sensor such as an ultrasonic sensor or optical sensor, or an imaging device (such as a camera). In this case, when the detector 250 detects that the nozzle assembly 205 and the examinee approach each other more than necessary, the controller 80 may perform an approach avoidance operation on the examination device 100, and switch the operation mode from a first mode where the approach avoidance operation is performed to a second mode where the approach avoidance operation is not performed.

In the above embodiment, the controller 80 may switch the operation mode from the first mode to the second mode when detecting contact more than once. For example, the controller 80 detects contact between the examinee and the nozzle assembly 205 and performs the avoidance operation in the first mode, and then performs a measurement again in the first mode. The controller 80 may switch the operation mode from the first mode to the second mode when detecting contact between the examinee and the nozzle assembly 205 for the second time.

In the above embodiment, in terms of measurement of the same examinee, the second mode is maintained. In terms of this, the first mode can be set again for each eye.

The approacher that approaches the examinee is not limited to the nozzle assembly and may be, for example, a test window (cover glass) of the examination device 100, an objective lens, an optical attachment, or other portions having a shape protruding toward the examinee.

The controller 80 may cause the ophthalmic apparatus 1 to execute the above processes illustrated in FIG. 4, which are stored in the storage 84.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An ophthalmic apparatus for examining an examinee's eye, comprising: an examination device configured to examine the examinee's eye; an approacher in the examination device, configured to approach the examinee; a detector disposed on the approacher and configured to detect approach of the approached to the examinee; and a controller configured to switch an operation mode between a first mode where an avoidance operation for avoiding the approach is performed and a second mode where the avoidance operation is not performed, upon the detector detecting the approach; where the approacher is a nozzle assembly including a nozzle and a nozzle holder.

2. The ophthalmic apparatus according to claim 1, wherein the detector is a contact sensor that detects contact between the approacher and the examinee.

3. The ophthalmic apparatus according to claim 1, wherein the controller switches the operation mode from the first mode to the second mode after, in the first mode, the detector detects the approach and the controller performs the avoidance operation.

4. The ophthalmic apparatus according to claim 1, wherein the controller notifies that the operation mode is to be switched from the first mode to the second mode.

5. The ophthalmic apparatus according to claim 1, wherein the controller displays, on a display, information that the operation mode is to be switched from the first mode to the second mode.

6. The ophthalmic apparatus according to claim 1, wherein the controller causes an audio output device to announce that the operation mode is to be switched from the first mode to the second mode.

7. The ophthalmic apparatus according to claim 1, wherein the controller switches the operation mode from the first mode to the second mode on the basis of operation input from an operating device operated by an examiner.

8. The ophthalmic apparatus according to claim 1, wherein the controller notifies that the detector has detected the approach in the second mode.

9. The ophthalmic apparatus according to claim 1, wherein the controller switches an alignment mode from an Auto mode to a manual mode after the detector detects the approach.

10. The ophthalmic apparatus according to claim 1, wherein the controller returns the operation mode from the second mode to the first mode after examination of the examinee's eye is finished.

11. The ophthalmic apparatus according to claim 1, wherein the controller returns the operation mode from the second mode to the first mode after examination of both eyes of the examinee is finished.

12. A recording medium where an ophthalmic apparatus control program to be executed in an ophthalmic apparatus for examining an examinee's eye is recorded, the program being executed by a processor of the ophthalmic apparatus to cause the ophthalmic apparatus to execute:

a detection step of detecting, by a detector, approach of an approacher to the examinee, the approacher being configured to approach the examinee in an examination device configured to examine the examinee's eye, the detector being disposed on the approacher; and a control step of switching an operation mode between a first mode where an avoidance operation for avoiding the approach is performed and a second mode where an avoidance operation for avoiding the approach is performed and a second mode where the avoidance operation is not performed, upon detecting the approach in the detection step.

13. The ophthalmic apparatus according to claim 1, wherein the detector is a capacitance sensor.

14. The ophthalmic apparatus according to claim 13, wherein the detector is electrically connected to the nozzle holder via a wire.

15. The ophthalmic apparatus according to claim 1, wherein the controller is configured to:
perform an alignment of the approacher with the examinee;
move the approacher away from the examinee when the detector detects the approach during the alignment under the first mode; and
move the approacher toward the examinee when the detector detects the approach during the alignment under the second mode.

* * * * *